United States Patent [19]

Sengpiel et al.

[11] Patent Number: 5,061,296
[45] Date of Patent: Oct. 29, 1991

[54] AIR PURIFICATION SYSTEM

[75] Inventors: William T. Sengpiel, Oak Brook, Ill.; Philip J. Doucet, Andover, Mass.

[73] Assignee: CRS Industries, Inc., Tampa, Fla.

[21] Appl. No.: 495,955

[22] Filed: Mar. 20, 1990

Related U.S. Application Data

[63] Continuation-in-part of Ser. No. 278,530, Dec. 1, 1988, abandoned.

[51] Int. Cl.⁵ .................................................. B03C 3/00
[52] U.S. Cl. ........................................... 55/4; 55/6; 55/105; 55/139; 55/126; 55/106
[58] Field of Search ............... 55/124, 126, 150-152, 55/136-138, 105, 106, 4, 6, 139

[56] References Cited

U.S. PATENT DOCUMENTS

| | | | |
|---|---|---|---|
| 3,040,497 | 6/1962 | Schwab | 55/112 |
| 3,626,668 | 12/1971 | Cardiff | 55/139 |
| 3,892,544 | 7/1975 | Haupt | 55/124 |
| 3,973,927 | 8/1976 | Furchner et al. | 55/136 |
| 4,164,901 | 8/1979 | Everett | 55/137 |
| 4,261,712 | 4/1981 | Kinkade | 55/126 |
| 4,477,263 | 10/1984 | Shaver et al. | 55/6 |

FOREIGN PATENT DOCUMENTS 251087A 11/1987 Fed. Rep. of Germany.

Primary Examiner—Bernard Nozick
Attorney, Agent, or Firm—Finnegan, Henderson, Farabow, Garrett and Dunner

[57] ABSTRACT

An air purification system for subjecting air to a complex electrical field including sensors and a monitor/controller for monitoring effectiveness, operational conditions of the electrical field and the system, and ambient conditions of the air being purified. The level of the high voltage, RMS and high frequency is processed so that frequency, RMS and high D.C. can be measured at a low D.C. voltage.

20 Claims, 9 Drawing Sheets

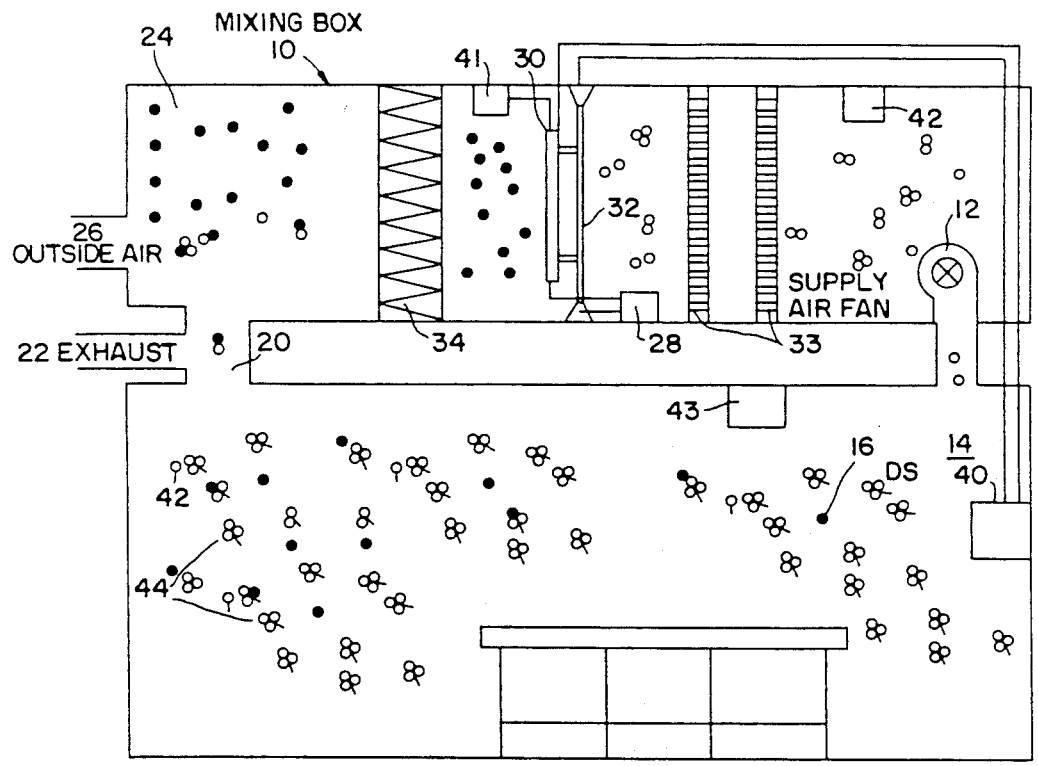
FIG. I
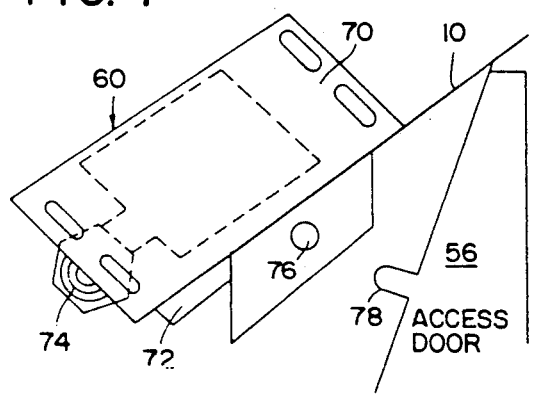
FIG. 4
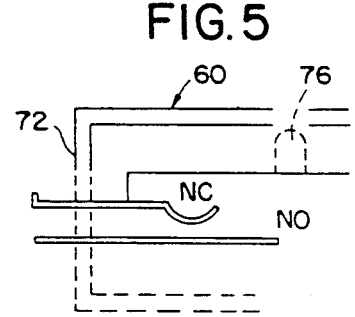
FIG. 5

5,061,296

AIR PURIFICATION SYSTEM

BACKGROUND OF THE INVENTION

This is a continuation-in-part of Ser. No. 07/278,530 filed Dec. 1, 1988 now abandoned.

The present invention relates to air purification systems and related method; and more particularly to an air purification system of the type that enhances filtration by subjecting airborne contaminants to complex electrical fields.

Air purification systems of the type under consideration include a fixed output power generator that produces both a high voltage (HV) direct current and a high frequency (HF) alternating current, the HV and HF output from the power generator is fed to separate electrodes. In large installations, electrodes are typically installed in an air handling plenum, usually between a filter and cooling coils, for example. The power generator is located nearby outside the air plenum. In operation, the HV and HF output generates a complex electrical field at the electrodes assembly; all of the air passing through the space being conditioned by the system, passes through this complex electric field during secondary air recycling. This changes the polarity of airborne particles altering their behavior, which tends to naturalize the space charge. By reducing the space charge in the conditioned space, it allows the submicron particles to adhere to each other increasing their mass instead of plating out on vertical, horizontal, inverted surfaces, people and machinery. As these particles become large enough to become airborne they are easily carried by the system air flow back through the return to be captured in the filters. The system thereby enhances filtration and removal of airborne particles and gasses thus reducing dust, smoke, and odor in an conditioned environment.

As a result, air purification systems of this type, save energy dollars by reducing the need for large amounts of outside air, saves initial investment dollars by reducing heating and cooling equipment requirements, saves day-to-day cleaning and maintenance of the air handling equipment and the conditioned space. Also, air purification systems of this type, control the offensive dust, smoke and odor, and increase human efficiency by restoring fresh, clean air to the interior environment where we live, work and breathe.

These systems operate effectively without any exterior noise, except perhaps that of an air handling fan, and also out of sight, thus rendering it difficult for anyone to detect immediately any interruption in the operation of the purification by the system. Therefore, presently, in systems of this type, the power generator is equipped with an indicator such as a light emitting diode to monitor and signify that the generator is turned on and electrically intact.

In air purification systems of this type where contaminents are subjected to a complex electrical field as part of the purification process, many ambient and system parameters influence the efficiency and effectiveness of the system.

Although the failure of the fixed output power generator can be detected in presently known systems, the effective operation of other components of the system or ambient conditions affecting and affected by the system cannot be readily detected. Thus, in the event of malfunction or change in operating conditions, the ineffectiveness of the air purification system can only be detected by the gradual recontamination of the air, thus causing discomfort; and reverting to conditions, which prevailed prior to the utilization of the air purification system itself. Further, inasmuch as a period of time is required, particularly in large installations, before an air purification system of this type can reduce the contaminents to the optimum level, any malfunctioning of the various parts of the system or change in operating conditions, may create an impure condition that takes several hours or days to be removed completely, even after such malfunctioning has been noticed and remedied.

SUMMARY OF THE INVENTION

One of the objects of the present invention, is to provide an air purification system and method that subjects air contaminents to a complex electrical field, with the capability of monitoring a change in the operation of the system and ambient operating conditions.

Another object of the present invention, is to provide such an air purification system and method that monitors the system operation and ambient conditions with the capability of varying the operation thereof.

Additional objects and advantages of the invention will be set forth in part in the description which follows, and in part will be obvious from the description or may be learned by practice of the invention. The objects and advantages of the invention may be realized and obtained by means of the instrumentalities and combinations particularly pointed out in the appended claims.

To achieve the objects and in accordance with the purpose of the invention, as embodied and broadly described herein, the air purification system of the present invention comprises means for flowing the air to be conditioned; a power generator including first means for generating a direct current having a selected voltage output and second means for generating an alternating current having a selected high frequency output; electrode means disposed in the air flow and electrically connected to the first and second power generating means for creating a complex electrical field; sensing means for detecting system and ambient conditions, and means responsive to the sensing means for monitoring the operational condition and effectiveness of the system.

In another aspect, the air purification system of the present invention includes monitoring means responsive to the sensing means for varying the operation of the system.

The accompanying drawings which are incorporated in and constitute a part of this specification, illustrate one embodiment of the invention and together with the description, serve to explain the principles of the invention.

BRIEF DESCRIPTION OF THE DRAWINGS

FIG. 1 illustrates the arrangement of the individual parts of an air purification system relative to the area being purified together with a diagramatic illustration of the atomic cohesion of the airborne contaminents;

FIG. 4 is a view in perspective of the safety door switch utilized in the system of the present invention illustrating its disposition in an air plenum relative the access door;

FIG. 5 is a view in elevation of the safety door switch of FIG. 4;

DESCRIPTION OF THE PREFERRED EMBODIMENT

Figure 2:
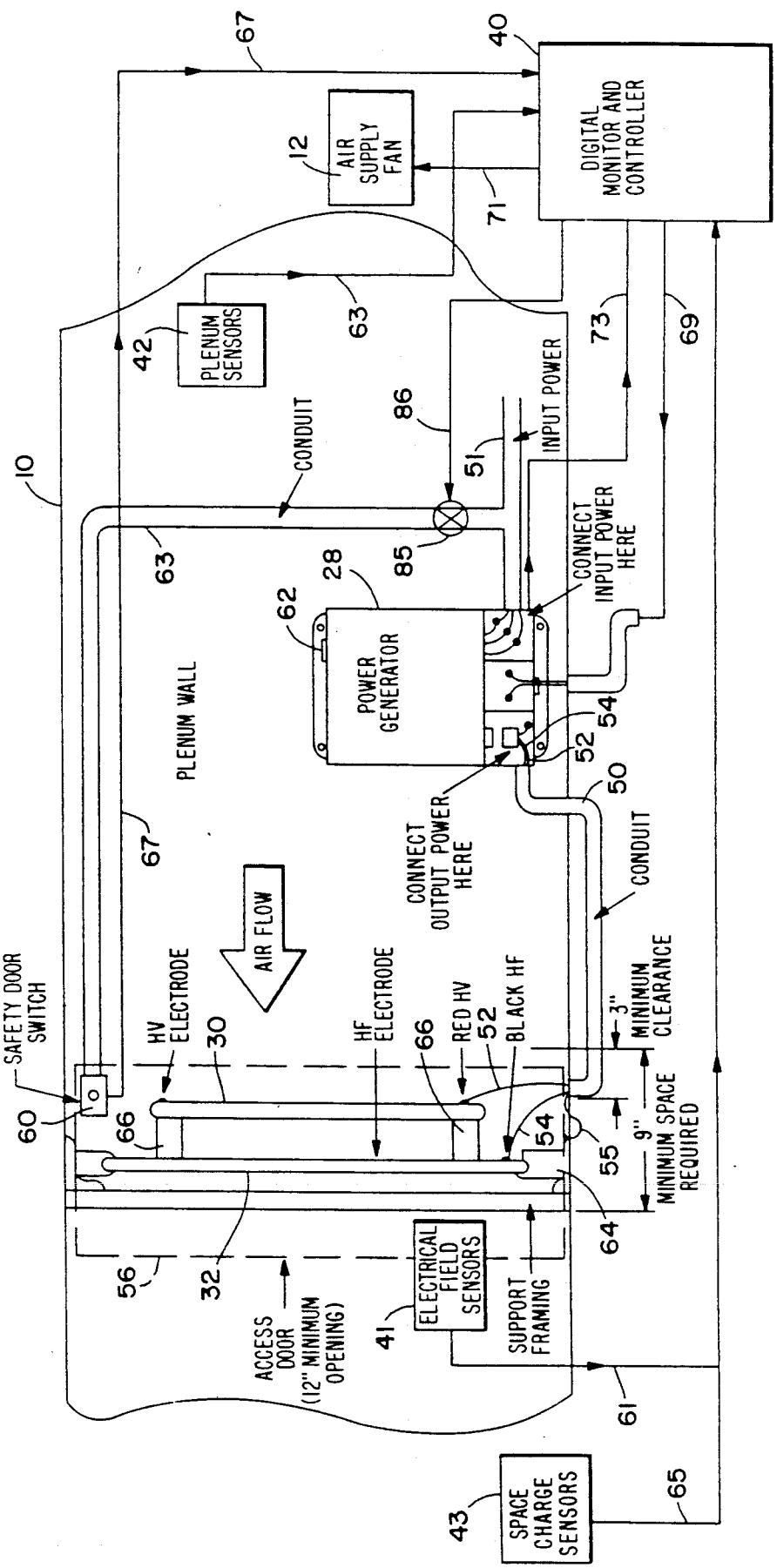
FIG. 2 is a schematic diagram illustrating the arrangement and connection of the individual components of the system together with the sensors and a remote digital monitor/controller; and a power generator mounted exterior to the plenum.

Reference will now be made in detail of the present preferred embodiment of the invention, an example of which is illustrated in the accompanying drawings.

Referring to FIG. 1, an air purification system of the present invention comprises a means for flowing the air to be conditioned or purified. As embodied herein, an air plenum 10 that includes a supply air fan 12 flows the air into a room generally referred to at 14. The flowing air, which includes contaminents such as 16, is circulated through a passage 20 where a certain portion of the air is exhausted through outlet 22 and another portion of which enters a mixing portion 24 of air plenum 10 which mixes with outside air through inlet 26. The contaminated air is then drawn through a filter 34. Although, the air purification is described in connection with a conditioned space having an air plenum, it is understood that the conditioned purified air may discharge into the atmosphere, as in an exhaust stack or air purge system.

The present invention includes a power supply generator that includes first means for generating a direct current and may have a variable high voltage output. It also has a second means for generating an alternating current and may have a variable high frequency output. As embodied herein, power generator 28 is disposed a predetermined distance outside of air plenum 10 and is operative to generate a direct current and an alternating current having a selected high voltage and frequency respectively.

The present invention includes electrode means disposed in the air plenum and electrically connected to the first and second power generating means for creating a complex electrical field from the direct current and alternating current outputs. As embodied herein, the electrode means comprises a high voltage electrode 30 and a high frequency electrode 32 which may be in the form of closely meshed metallic screens that are spaced and insulatively connected to one another. The electrodes may include movable grids or selectively engaged areas for controlling the degree of treatment. It is understood that the electrode means may also be in the form of any or all conductive wire mesh; rods, braided, or other types of wire in other geometric configurations.

In accordance with the invention, sensing means for detecting system and ambient conditions, and means responsive to the sensing means for monitoring the operative condition and effectiveness of the system are also included in the system. As embodied herein, such sensing means preferably includes a plurality of distinct sensor types such as 41, 42 and 43 (see FIG. 1) mounted at appropriate locations in air plenum 10 and space 14 for sensing respective operating conditions of the system and ambient conditions of the space being conditioned, or air being exhausted.

As, illustrated, the system of the present invention also includes air filter 34 mounted in air plenum 10 upstream of electrodes 30 and 32 and cooling or heating coils 38 mounted in plenum 10 downstream of electrodes 30 and 32.

As embodied herein, the system of the present invention also includes a digital monitor/controller 40 for detecting and processing the sensed conditions of the system and the environment as described in more detail hereafter.

With reference to FIG. 1, as the air passes through the complex electrical field generated at the assembly of electrodes 30 and 32, smaller particles begin to coalesce rapidly as indicated at 48 between electrode 32 and coil 38. These small particles grow larger and larger as they pass through the conditioned space to the return air at passage 20 as indicated by clusters and 44 for example. Thus, the system of the present invention causes a shift in particle size in the conditioned space from fine, difficult to collect particles, to larger more collectible particle sizes. In one test, it was shown that there was a 367% increase in large particle mass and 94% of the particle mass involved in the shift was removed from the conditioned area. These large particle clusters such as 42 and 44 are then either exhausted through opening 22 or mixed with dirty untreated outside air through inlet 26 in the mixing box 24 and readily collected by the medium or high efficiency filters 34. For most applications, such filters may have an efficiency rating of approximately 55% and other more restricted applications such as data processing centers, should have filters 34 with an efficiency in the neighborhood of 80%. The filtered air, which still contain millions of fine particles, then passes through electrodes 30, and 32, and the purification cycle begins again, significantly reducing the airborne dust, smoke, gases and odors in the conditioned space.

Figure 3:
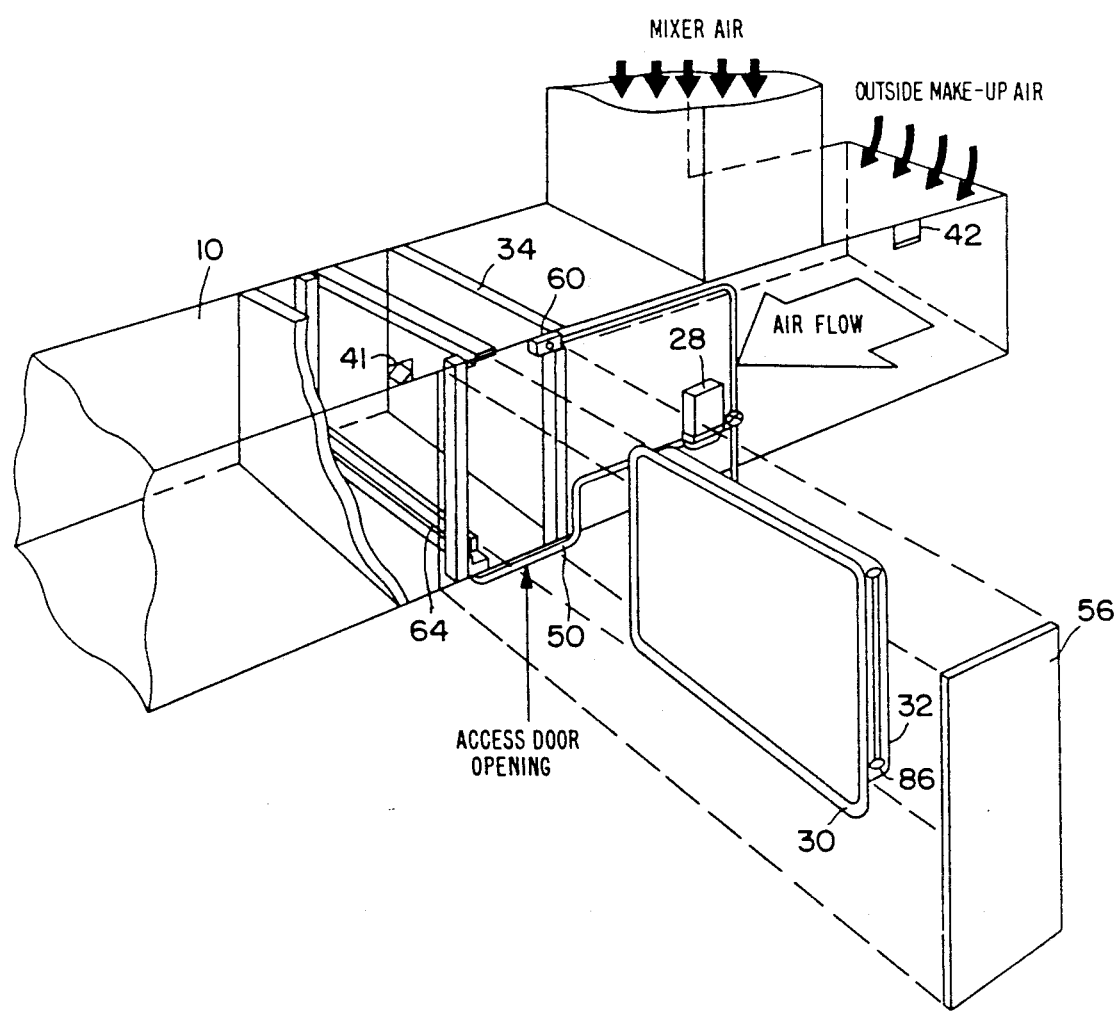
FIG. 3 is a view in perspective of the air purification of the present invention illustrating the manner of removably mounting an electrode assembly in the air plenum.

Referring to FIGS. 2 and 3, air plenum 10 includes a door 56 that permits access to electrodes 30 and 32 for inspection or replacement. A safety door switch 60 is mounted on door 56 for shutting off the power to generator 28 when the door is open. It is preferable that power generator 28 be mounted as closely as possible to electrodes 30 and 32. Unsatisfactory operation has been noticed at times when the power generator is mounted more than 10 ft. from the electrodes. Power generator 28 should also be mounted on the exterior plenum wall of air plenum 10. Power generator 28 has louvers 62 for maintaining proper air circulation therethrough during operation. High frequency electrode 32 is mounted in air plenum 10 by support framing 64, and electrode 30 is spaced from and insulatively attached to electrode 32 by spacers 66. As previously mentioned, these electrodes in the plenum consist of mechanisms necessary to create complex electrical fields in order to modify ion balance, surface charge, and molecular structure of air passing through them. The electrodes may consist of fixed grids of conductive mesh, rods, braided or other type wire in other geometric configuration, as well as movable grids controlled by signals from digital controller 40.

Referring to FIG. 3, electrodes 30 and 32 may be removed from air plenum 10 by opening access door 56 and sliding them from the support track out of the plenum. The electrodes 30 and 32 together with support framing 64 are fabricated to fit the clear internal plenum or duct dimensions so that all of the air flowing in the air plenum passes through electrodes 30 and 32.

Application experience with the generated complex electrical field, has provided a clear set of criteria under which the system operates most effectively and efficiently. For example, for optimum operation, outside air in the amount of 10% is continuously brought in to the mixing box for conditioning. For applications where large numbers of people are present, it has been found that the recommended intake of outside air into the enclosed space should be in the neighborhood of 5 cubic feet per minute for each person. Additionally, for optimum control of irritants and odors, the conditioned space such as room 14 should be maintained below 60% relative humidity and between 60° F. to 80° F. (dry bulb).

Further for proper operation, the average face velocity through the electrodes 30 and 32 should not exceed 850 ft. per minute, for example, with a uniform velocity profile maintained through the electrode assembly at all times. Also, the electrodes preferably should not be utilized in relative humidity conditions above 85%. Additionally, there are various assembly requirements for the system which influences its effective operation. For example, in one practical embodiment and regardless of electrode size, at least 9 in. of unobstructed space in the direction of air flow for the electrodes support framing and all necessary clearances, are required. Pressure or thermosensing devices used in the present invention are not to be mounted in the 9 in. of clear space provided for the electrode assembly 30, 32. On air plenums that are internally insulated, a minimum 9 in. sheet metal internal liner should be installed in the electrode area. For slide-out electrode assembly arrangements as shown in FIG. 3, the access door opening for door 56 is preferably at least 12 in. wide, centrally located relative to support track 64 and of adequate height to allow removal of electrodes 30, 32. For filters which can be replaced from the downstream side in the direction of air flow, common access may be used for both electrodes 30, 32 and the filter. If, however, filters are installed from the upstream side, as shown in FIGS. 1 and 3, separate access should be provided for the filters. Safety door switch 60 is located inside each plenum access door 56 as shown in FIG. 4. Switch 60 has a mounting bracket 70 and a switch portion 72 having an inlet 74 for the conduit from power generator 28. Switch portions 72 has a button 76 that is engaged by a protrusion 78 on the access door for cutting off the power to power generator 28 when the door is not completely closed. FIG. 5 shows the connection from switch portion 72 to power generator 28. The wiring of switch portion 72 into the line voltage circuit interrupts input power to the power generator 28 when any access door such as 56 is opened. A minimum of 3 in. clearance is preferably maintained between the electrodes 30, 32 and safety door switch 60 to prevent any malfunction of the electrodes. Preferably, switch portion 72 is an enclosed, carryover, snap action type single throw switch with a minimum of 5 amps for power generator 28 with a conventional 125 A.C. voltage rating. Bracket 70 is designed so that the switch portion 72 can only be activated by the properly positioned special protrusion or plunger 78 provided as part of the safety door assembly.

Referring again to FIG. 2, power generator 28 is electrically connected at its output to high voltage electrode 30 by wire 52 and to high frequency electrode 32 by wire 54, both of which are enclosed by a conduit 50. A wire is connected through the ground post on the power generator from the same conduit 50 to a ground post on the angle support for the electrode assembly (not shown). Input power is connected to power generator 28 through conduit 51, which has a branch 53 through which extend the conductors connected to safety door switch 60. Electrical field sensor 41 is mounted in plenum 10 approximately six inches from high frequency electrode 30, the output of which is connected to an input of controller 40 over line 61. Sensors 42 for sensing the ambient conditions in air plenum 10 may be mounted near air supply fan 12 (see FIG. 1). The output of sensors 42 are connected to controller 40 over line 63. Sensors 43, which may be mounted in the room or space being conditioned for measuring the condition of the air, have outputs connected over line 65 to controller 40. Electrodes 30 and 32 are electrically connected to an electrode detecting monitoring means (see FIGS. 8–12) for determining the actual characteristics of the voltages and frequency applied to the electrodes. Although safety door switch 60 operates to interrupt the input power to generator 28 as previously explained, it may also have an output 67, which indicates the position of door 56 to controller 40 for controlling other equipment such as air supply fan 12. Controller 40 has an output 69 connected to power generator 28 and an output 71 connected to fan 12 for varying the respective operations thereof in accordance with the output from electrodes 30 and 32, and from sensors 41, 42, and 43. Primary power from generator 28 is also monitored by controller 40 through line 73, and the controller can shut off the primary power at switch 85 over line 86.

Primary power (120 VAC) is internally monitored by controller 40 since variations can affect HV and HF generator outputs. Service access door(s) and supply fan interlocks are used to turn off HV and HF power generators when unit is opened for service. By monitoring the interlock signals and electrodes, the monitor/controller 40 provides an alarm if high voltage and/or high frequency do not exist when the power generators should be operating.

In accordance with the invention, the electrode detecting and monitoring means comprises a first circuit means for generating a first output A.C. signal having an RMS amplitude corresponding to a predetermined fraction of the electrode HF voltage and a second output D.C. signal having an amplitude corresponding to a predetermined fraction of the electrode HV output.

Figure 8:
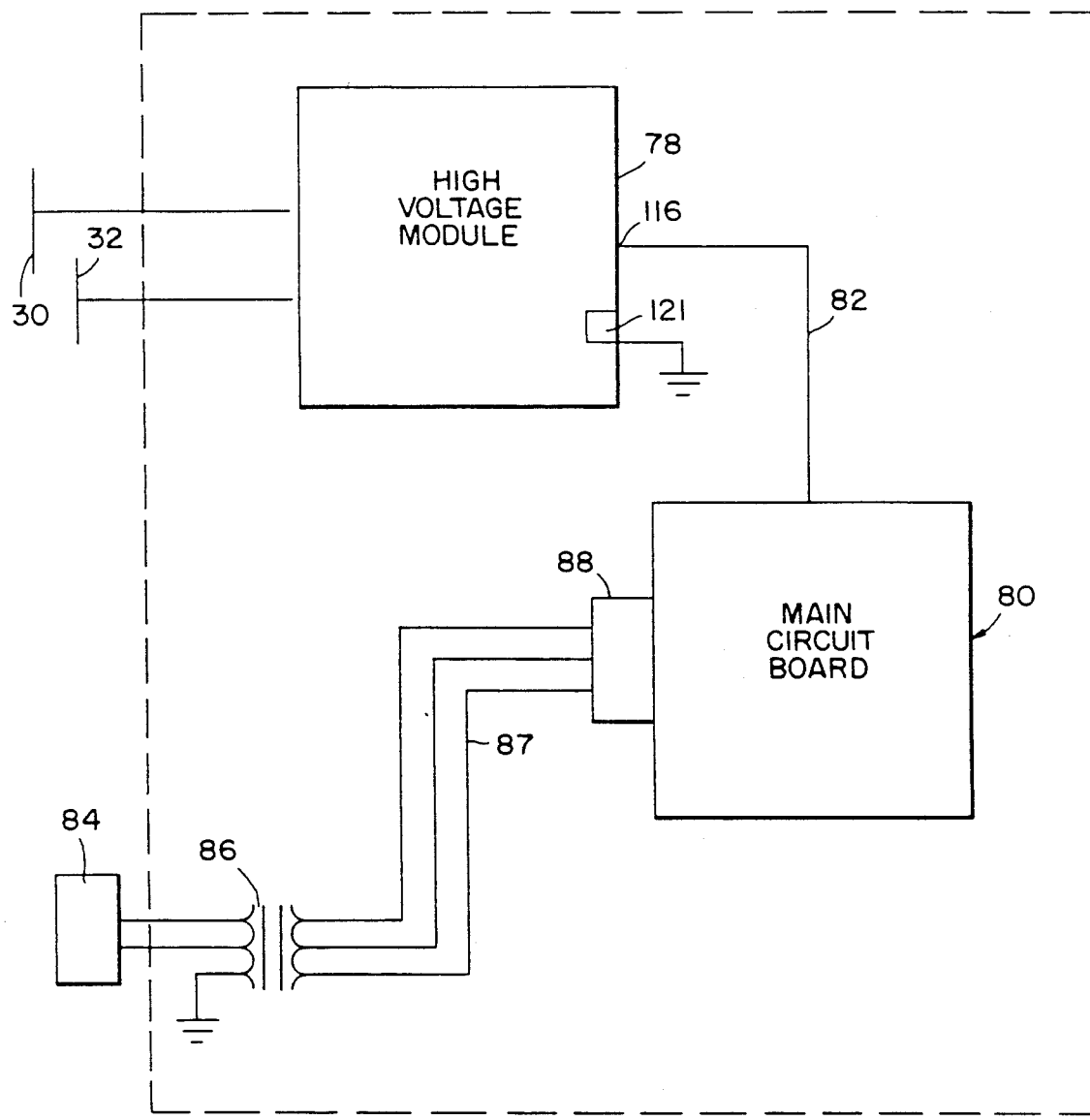
FIG. 8 is a block diagram of the electrode electrical field sensors of the present invention.

As embodied herein and referring to FIG. 8 the first circuit means comprises a high voltage module 78 with a connector 92 connected to electrodes 30 and 32 for generating a first output A.C. signal and a second output D.C. signal on multiple conductor bus 82. The electrode detecting and monitoring means also comprises a second circuit means including a first converter means responsive to the first output signal for generating a first D.C. signal having a voltage value corresponding to the RMS voltage of the first output signal, and a second converter means for generating a second D.C. output signal having a voltage value corresponding to the frequency of the HF voltage.

As herein embodied and referring to FIG. 8, the second circuit means comprises a main circuit board 80 with bus 82 from module 78 connected thereto. Power for main circuit board 80 is provided by a 120 volt A.C. source through stepdown transformer 86 which reduces the voltage to twenty volts, a cable 87, and a plug 88 which is removably insertable into corresponding sockets 90 of circuit board 80. Thus, the electrode detecting and monitoring means detects the electrode voltages in the kilovolt and kilohertz ranges and converts them to D.C. signals in the 0–2 volt range. These signals, may be applied to a socket such as 90 for local monitoring and read out or to a terminal strip, for connection to a remote read out, or monitoring system.

Figure 9:
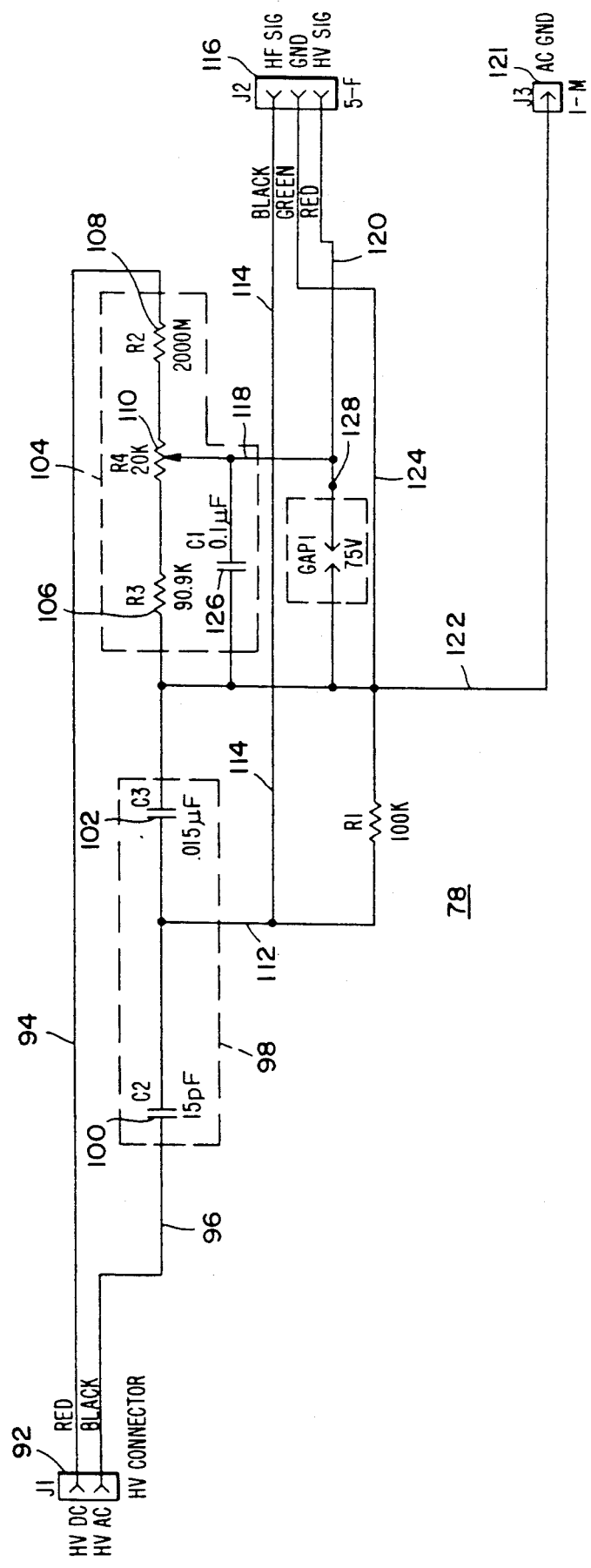
FIG. 9 is a schematic circuit diagram of the high voltage module of the electrode sensor of FIG. 8.

As herein embodied, and referring to FIG. 9, high voltage module 78 comprises a voltage divider 98, a voltage divider 104, and a spark gap 128. The high frequency A.C. voltage from electrode 32 is input on wire 96 to voltage divider 98, which includes a capacitor 100, preferably 15 pico farads, and a capacitor 102, preferably 0.015 micro farads connected in series with capacitor 100. Voltage divider 104 is connected at an input end to wire 94, which is directly connected to high voltage electrode 30. Voltage divider 104 includes a resistor 106, which is preferably 90.9 kilohms, a series connected resistor 108, which is preferably 2,000 megohms, and a trimming resistor 110 connected between resistors 106 and 108, which preferably has a minimum resistance of twenty kilohms. The reduced A.C. voltage from divider 98, which corresponds to the voltage on high frequency electrode 32, is output over wire 112 and wire 114 to connector 116 for connection to multiple conductor bus 82 (FIG. 8). The reduced D.C. voltage from divider 104, corresponding to the voltage on the high D.C. voltage electrode, is output over wire 118 and wire 120 to connector 116 for connection to multiple wire bus 82. Ground reference 121 for both dividers 98 and 104 is connected by wire 122 to the output of voltage divider 98 and through blocking capacitor 126 to wire 118, the output of divider 104. Spark gap 128, which is connected to connector 116 in parallel with capacitor 126, limits the voltage in the line to approximately 75 volts in the event of a breakdown in voltage divider 104.

The maximum high frequency signal on electrode 32 is approximately a 3,000 volt peak-to-peak sine wave of 150 to 200 kilohertz. This signal is fed over wire 96 to voltage divider 98, which reduces the voltage to approximately 3 volts peak-to-peak; or in other words in the ratio of 1000 to 1. Capacitors 100 and 102 have a tolerance of approximately 1% with excellent temperature and frequency characteristics.

The maximum voltage on electrode 30 is approximately 30,000 volts, and divider 104 is preferably a 20,000 to 1 divider, thus reducing the voltage to a maximum of approximately 1.5 volts. Since the trimming resistor 110 is rated preferably at 20,000 volts, it is capable of changing the total resistance by approximately three percent. Resistor 108 has a voltage coefficient in the neighborhood of plus or minus 1%. Accuracy at output 118-120 can be achieved over a range of about fourteen kilovolts, which should be considered in adjusting trimming resistor 110.

Thus, high voltage module 78 outputs a D.C. voltage signal in the range of approximately zero to 2 volts in accordance with the corresponding high D.C. voltage on electrode 30, and outputs an A.C. signal in the neighborhood of 3 volts in accordance with the voltage on electrode 32.

Figure 10:
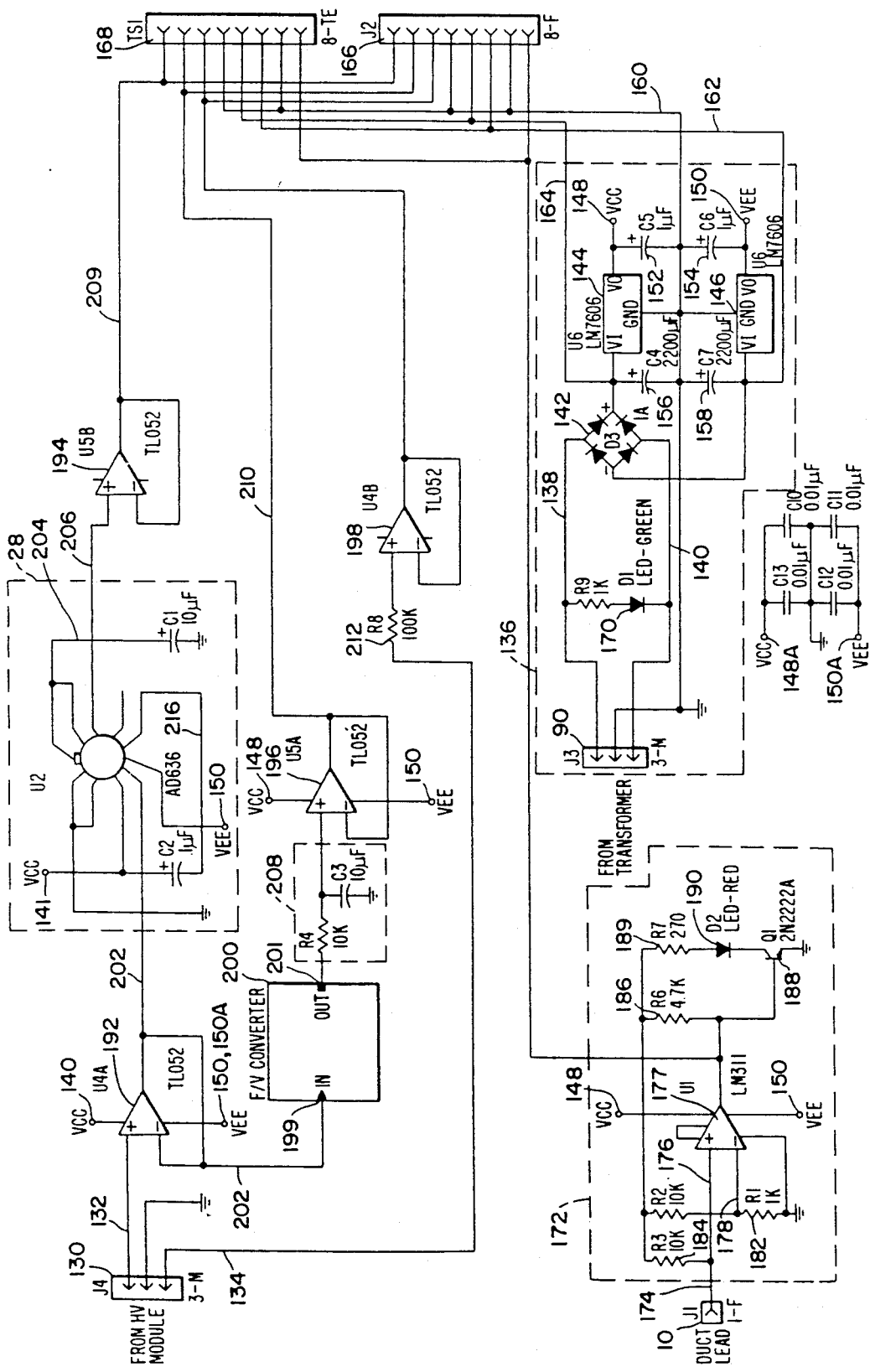
FIG. 10 is a schematic circuit diagram of the main circuit board of the sensor of FIG. 8.

The outputs of high voltage module 78 are transmitted over cable 82 to connector 130 of main circuit board 80. (FIG. 10). Connector 130 includes conductor 132 to which is connected conductor 114 of connector 116 of high voltage module 78 for inputting the low voltage A.C. signal corresponding to the high voltage of the HF electrode. Connector 130 also includes a conductor 134 connected to conductor 120 of connector 116 for inputting the low value D.C. voltage signal corresponding to the voltage on HV electrode 32.

In accordance with the invention, the electrode detector includes a second circuit means for generating a first D.C. signal having an amplitude corresponding to the RMS of the low voltage A.C. signal from module 78 and a second D.C. signal corresponding to the frequency of the low voltage A.C. signal from module 78. As embodied herein and referring to FIG. 10, the second circuit means comprises circuit board 80 which includes a power supply, duct ground tester, buffers, RMS converter for providing accurate low voltage D.C. outputs for the high voltage and high frequency electrodes. Circuit board 80 has a power supply generally referred to as 136, which includes connector 90, the input of which is the center tapped secondary coil of transformer 86 (see FIG. 8). The A.C. power is conducted over wires 138 and 140 to full wave rectifier 142 that feeds linear voltage regulators 144 and 146. The center tap of transformer 86 is connected to the ground connections of linear regulators 144 and 146, giving a positive output of five volts on terminal 148 and a negative output of five volts on terminal 150. The positive and negative power is filtered with 2200 microfarad capacitors 152, 154, 156, and 158, which are connected between ground and the respective inputs and outputs of each regulator 144 and 146. The ground connections from the power supply are provided over wires 160, 162, and 164 to the pins of eight pin connectors 166 and 168. Thus, large return currents will not affect signal levels. Light emitting diode 170 connected across conductors 138 and 140 indicates the presence of A.C. power in the transformer 86.

A duct ground tester 172 is provided for testing the resistance between ground and the A.C. power source of power generator 28 (see FIG. 2) Circuit ground is made only through connection 121 (FIG. 9) of high voltage module 78. This is done because high voltage D.C. signals on HV electrode 30 and high voltage A.C. signals on HF electrode 32 are referenced to the A.C. power ground in power generator 28. A duct lead 174 is electrically connected to duct 10 (FIG. 2) and to an input 176 of comparator 177. Input 178 of the comparator is connected through a one kilohm resistor 182 to the A.C. power ground. Conductor 174 connected to duct 10 through connector 50, is also connected through a ten kilohm resistor 184 and a 4.7 k resistor 186 to a base of switching transistor 188. Conductor 174 is also connected through resistor 184 and a two hundred seventy ohm resistor 189 to one terminal of a light emitting diode 190. If the duct to ground resistance on inputs 176 and 178 respectively is approximately 1000 ohms or greater, comparator 177 conducts, thus applying a negative voltage from terminal 150 to the base of transistor 188 which completes a circuit for lighting diode 190. If the resistance should fall below approximately one kilohm, then transistor 188 shuts off, and light emitting diode 190 goes out, indicating a current leakage between the duct and A.C. ground. Proper operation of the electrode assembly as well as safety considerations, such as leakage or shorts from electrodes 30 and 32 to duct 10, requires a grounded duct.

Main circuit board 80 includes high impedance buffers 192, 194, 196 and 198 for reducing the loading on high voltage module 78, which buffers are preferably FET operational amplifiers operating as unity gain followers. Operational amplifier 192 buffers the input signal corresponding to the HF voltage on conductor 132 and applies it to input 199 of frequency to voltage converter 200, and on conductor 202 to the input of a root mean square (RMS) to D.C. converter 204. Operational amplifier 194 is connected between output 206 of RMS to D.C. converter 204 and terminals 168 and 166, for buffering the D.C. output signal. Operational amplifier 196 is connected between a low pass filter 208 at the output of frequency converter 200 and terminal boards 166 and 168. Operational amplifier 198 is connected in line 134 between input terminal 130 and output terminals 166 and 168 for buffering the voltage from module 78 corresponding to the high voltage of HV electrode 30. A 100 kilohm resistor 212 connected in series with an input of operational amplifier 198 limits the current to amplifier 198 in case of failure in high voltage module 78.

Converter 204, which is preferably a monolithic RMS to D.C. converter converts the high frequency signal at line 202 to a D.C. signal at output 206 having an amplitude corresponding to the RMS of the high frequency signal. The buffered D.C. signal is output to terminal 166 and 168 over conductor 209. The output on line 206 is proportional to the RMS input with the feedback error in loop 216 depending on input level, frequency, and crest factor. A one volt RMS input (2.828 volt peak to peak) sine wave on line 202 produces one volt D.C. output at better than one percent accuracy up to 220 kilohertz on line 206.

Frequency to voltage converter 200 is provided to convert the HF signal to a D.C. voltage that varies between 0 and 2 volts as a function of the frequency of the buffered signal on line 202. As herein embodied and referring to FIG. 11, frequency to voltage converter 200 comprises a zero crossing detector 222, a Schmitt trigger nand gate 224, a nand gate 226, a 12 bit counter 228, and an eight bit d/a converter 230 to provide an analog on 201. Converter 200 also comprises an oscillator 232 which is preferably 3.579 MHZ, a 14 stage counter 234, a pair of J-K flip-flops 236 and 238, flip-flop circuit 240, and a four bit shift register 242.

The buffered high frequency signal at 199 is fed to zero crossing detector 222 which preferably has a 100 mV hysterisis provided by resistors 244, 246, and 248. Thus, no input signals will be detected that have less than 100 mV peak. The input signals are further conditioned by Schmitt trigger Nand gate 224, the output of which is connected to an input of Nand gate 226.

Oscillator 232 is used as a time base; and drives fourteen bit counter 235. Nand gate 252, has inputs connected to the final three stages of counter 235, and an output connected to input of Nand gate 254, the output of which resets the counter, which forms a divide by 14,336 on line 256 resulting in a clock frequency of approximately two hundred fifty-nine Hz. This resulting frequency is input through flip-flop 236 for an additional division by four resulting in a 62.42 Hz time lapse. Twelve bit counter 228 is clocked by the frequency of the signal to be measured. The high order eight bits of the counter are output to a d/a converter 230 whose full scale output is 2.56 volts. With the 62.5 Hz time base, a 256 kilohertz signal provides a full twelve bit count of 4095. The d/a converter output is therefore 1 volt per 100 KHz. Although an eight bit D/A converter is satisfactory, a 12 bit d/a converter can be used to obtain better resolution.

Four bit shift register 242 sequences the entire frequency to voltage converter circuit. It is initially in a "load" state with S/L terminal low to preset only stage A of register 240. Gate 226 is concurrently enabled to let the input signal clock counter 228. At the end of a measurement cycle flip-flop 240 changes state, causing gate 226 to cease conducting and setting S/L terminal high, shifting the single bit through register 242 by the clock 232 on line 260. Stage B of shift register 242 loads d/a converter latch through gate 262, and stage D resets counter 228 over line 264 and clears flip-flop 240 over line 266 to begin another measurement cycle.

Figures 11, 12:
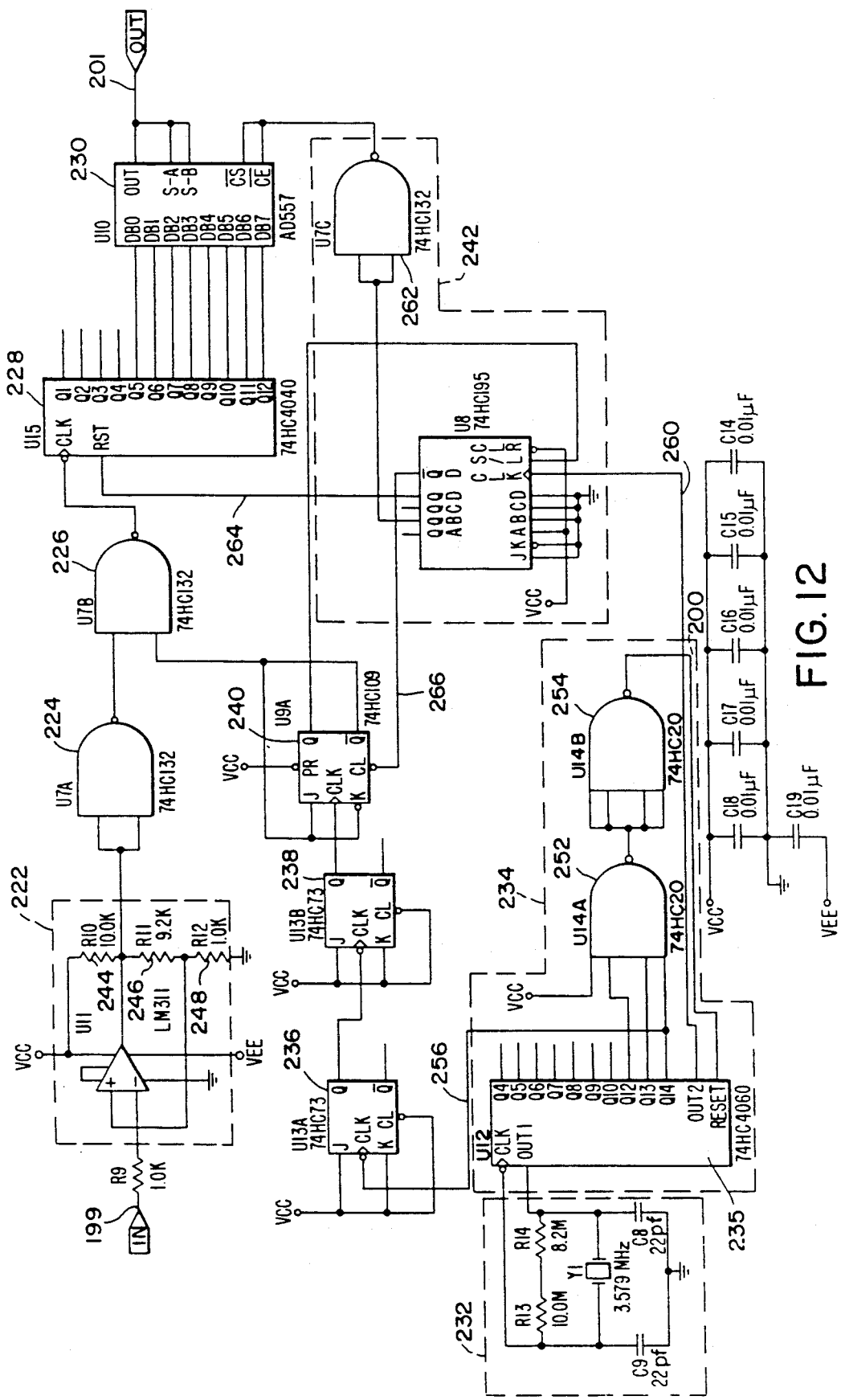
FIG. 11, is a schematic circuit diagram of the frequency to voltage converter of the main circuit board of FIG. 10.
FIG. 12 is a bypass circuit.

Referring to FIG. 12, terminals VCC and VEE are connected to corresponding terminals VCC and VEE of zero crossing detector 222, d/a converter 230, counter 235, Nand gates 252 and 254, and flip-flop circuit 242. Flip-flop circuits 236, 238, 240, Nand gates 224, 226, flip-flip circuit 242 including Nand gate 262, counter 235, 228, and D/A converter 230 require connection to the positive 5 volts power supply and ground.

Thus, the electrode detection and monitoring means measures the electrode voltage (kilovolts D.C.), the frequency (cycles per second) and RMS (root mean square) voltage to provide low voltage D.C. read-outs on monitor/controller display panel, as well as indicator lights, which verify operation of the HV and HF power generator. Controller 40 may have conventional multiplier devices for converting the low voltage D.C. signals to a read-out of the actual voltage levels. Also, controller 40 also may have an A/D converter so that the D.C. signal can be converted to a digital read-out of the actual frequency of HF electrode 32. This information may be input to a computer so that frequency and integrity can be established, and the output conditions from the power generator can be changed in the event the ambient conditions in the air stream cause the frequency to degrade or the output of the electrodes to degrade. By using the information in the computer, a consistent control band to produce the correct strength of field can be maintained to provide the desired contamination reduction performance.

Sensors 42, which may be of any well known type, may be mounted as previously outlined and measure duct air flow, temperature, and relative humidity to ensure correct operating conditions for the electrodes. The digital controller/monitor 40 may be set to alarm out-of-range conditions, or send an alarm signal to a remote location. The power generator may be turned off if alarm conditions require it.

Electrostatic charge sensors 43 of a conventional type, are mounted in the conditioned space as previously described, or at the discharge of a stack, and measure the beneficial effects of the system operation by reading the amount of space charge or surface charge at one or more locations in the conditioned space. According to one embodiment, as many as eight sensors may be monitored by the controller 40, and either the maximum or average reading can be used for triggering an alarm condition.

Thus sensors 41, 42, and 43 consist of means to measure the concentration of ions, particulates, and chemical composition of air in the air handling apparatus as well as in the space. Also the flow rate, and the wet and dry bulb temperatures of air flowing through the air handling apparatus and measure the electric field voltages, frequencies and other characteristics of the signals on the electrodes mounted in the air handling apparatus.

Controller/monitor 40 is preferably a microcomputer that controls and monitors the system. One controller 40 is used with each electrode assembly 30 and 32. The local digital read-out displays system performance, and all information can also be obtained at a central location by using a fiber optic network and central control station. It provides control of power generator 28, alerts operators of system inefficiencies and malfunctions, and simplifies the servicing of the system, all as previously outlined.

Figure 6:
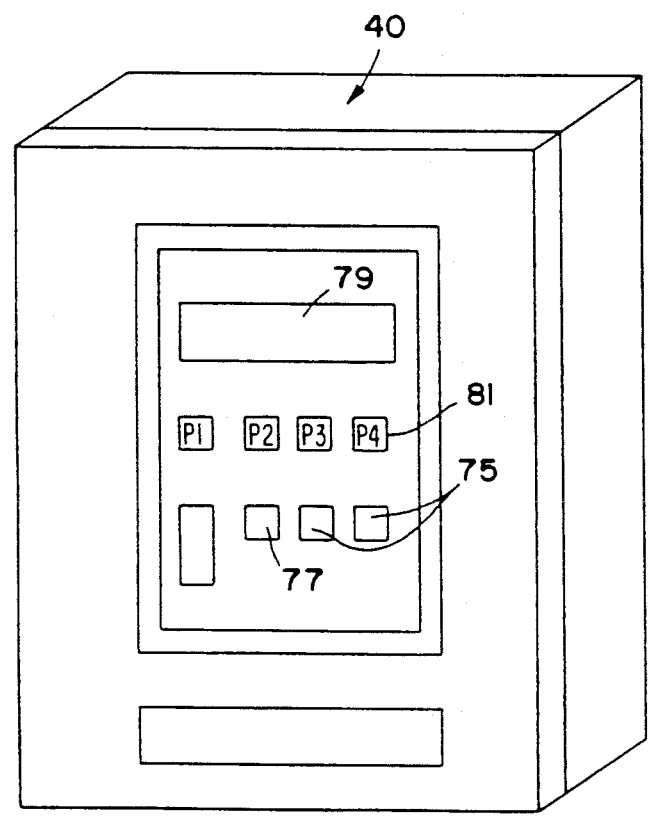
FIG. 6 is a view in perspective of the housing and indicators thereon for the digital monitor/controller in the system of the present invention; [and]

Digital controller/monitor 40 has a 120 VAC two amp. input and may also supply power to several power generators. It preferably is constructed to have fifteen analog inputs consisting of three inputs for electrode sensors 41 and twelve inputs for sensors 42 and 43 responsive to conventional 0-5 or 0-10 volt or 4-20 mA transmitter, including space charge, duct temperature, duct relative humidity and duct air flow. Also two digital inputs are provided for service access door state and air supply fan state. Referring to FIG. 6, controller 40 includes indicators 75 high voltage and high frequency in the ON state. Indicator 77 for door closed, and on LCD read-out 79 that includes two lines of twenty-four characters each to display selected parameters or combinations of parameters such as the frequency, RMS, and high D.C. voltage heretofore discussed. Function buttons 81 may be operated in various combinations to select different read-outs, set alarm points, and trouble shoot the installed condition and operation of the system. Controller 40 also embodies appropriate control processes in software and firmware that can vary power generator signals to the electrodes, as well as mechanical configuration of the electrodes, to satisfy static charge and particulate size, type and concentration requirements in the space and in the air handling apparatus itself.

The power generators develop complex high voltage and high frequency signals for powering the electrodes. The specific voltages, frequencies and other signal characteristics may be determined by data in the digital controller. The power generators have the ability to vary their outputs in response to signals from the controller. Power generator outputs can be varied to include, but are not limited to, D.C. voltage, A.C. voltage, A.C. frequency, swept A.C. frequency, D.C. pulse. D.C. pulse output may include variable polarity frequency, duty cycle, rise time, and fall time.

Figure 7:
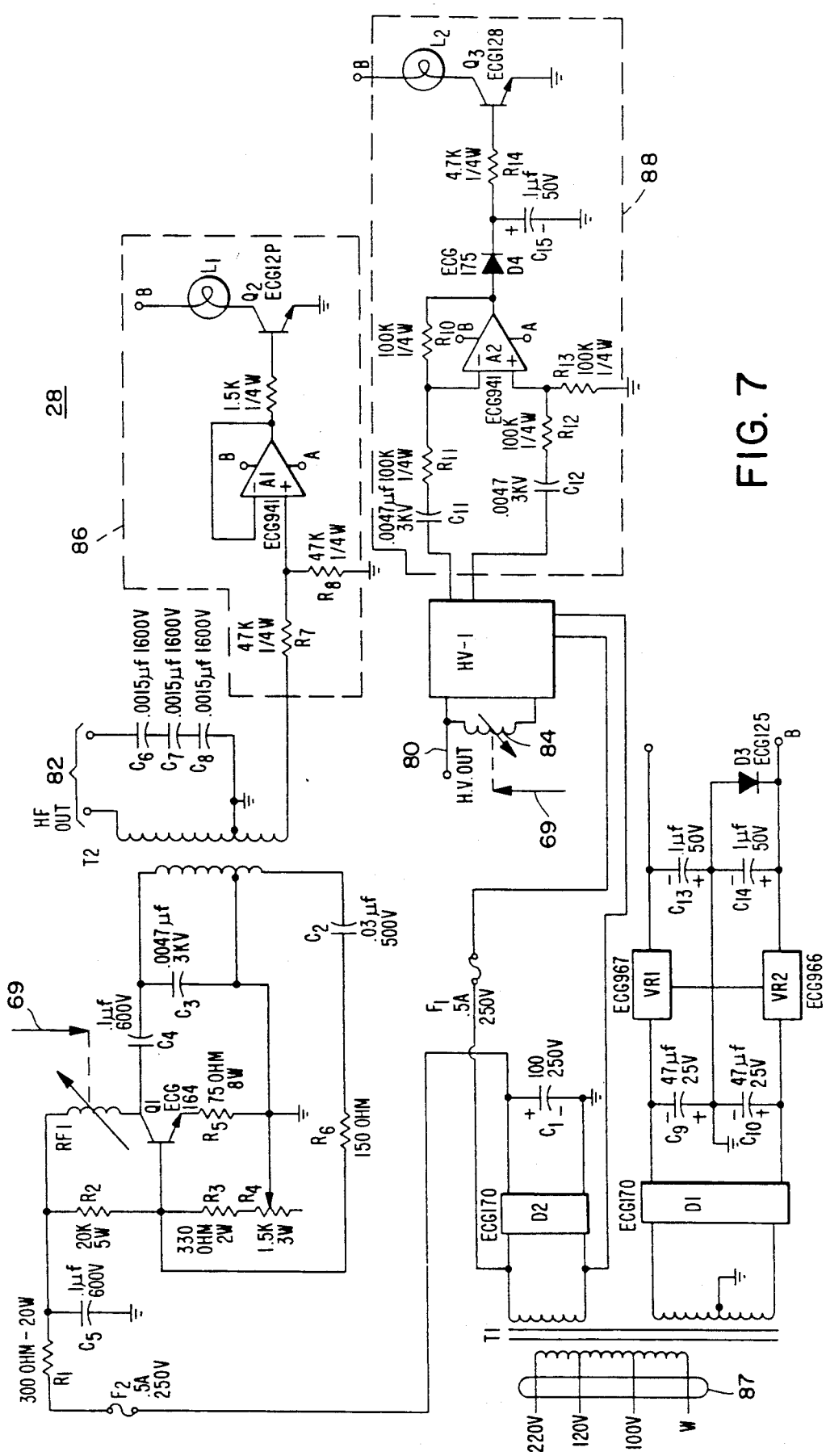
FIG. 7 is a circuit diagram of the power generator that may be used in the system of the present invention.

Referring to FIG. 7, power generator 28 may have a variable high voltage output from 22,000 to 28,000 volts with a range of 10% at 10 microamps at output 80, a high frequency output at bus 82 is in the range of 500 Hz to 600 MHz at 350 microamps. The input voltage may be either 90/100, 110/120, or 220/240 volts A.C. at 50 to 60 Hz single phase as shown at primary winding 87 of transformer T1. Input power is a 50 watt maximum for each power generator 28.

Transformer T1 is connected to rectifier bridges D1 and D2. Bridge D2 is connected to a voltage multiplier HV-1 for producing the (HV) direct current. Voltage regulator VR1 and VR2 are provided at the output of rectifier bridge D1. Rectifier Bridge D2 is also connected through RF coil RF1 and transformer T2 to produce the (HF) frequency. Coil RF1 is illustrated as capable of providing adjustment for varying the frequency in response to controls and over line 69 from monitor/controller 40. A symbolic variable resistance is illustrated at 84 for varying the (HV) voltage output, which may be controlled by monitor/controller 40 over line 69. Circuit portions within dashed lines 86 and 88 include indicators L1 and L2 for detecting the frequency and voltage output of power generator 28.

The maximum plenum cross-sectional area, or in other words, the electrode face area should not exceed 60 sq. ft for each generator. For large application where more than one electrode assembly is used, their corresponding power generators can be selectively turned on or off depending on the degree of air contamination.

Figure 13:
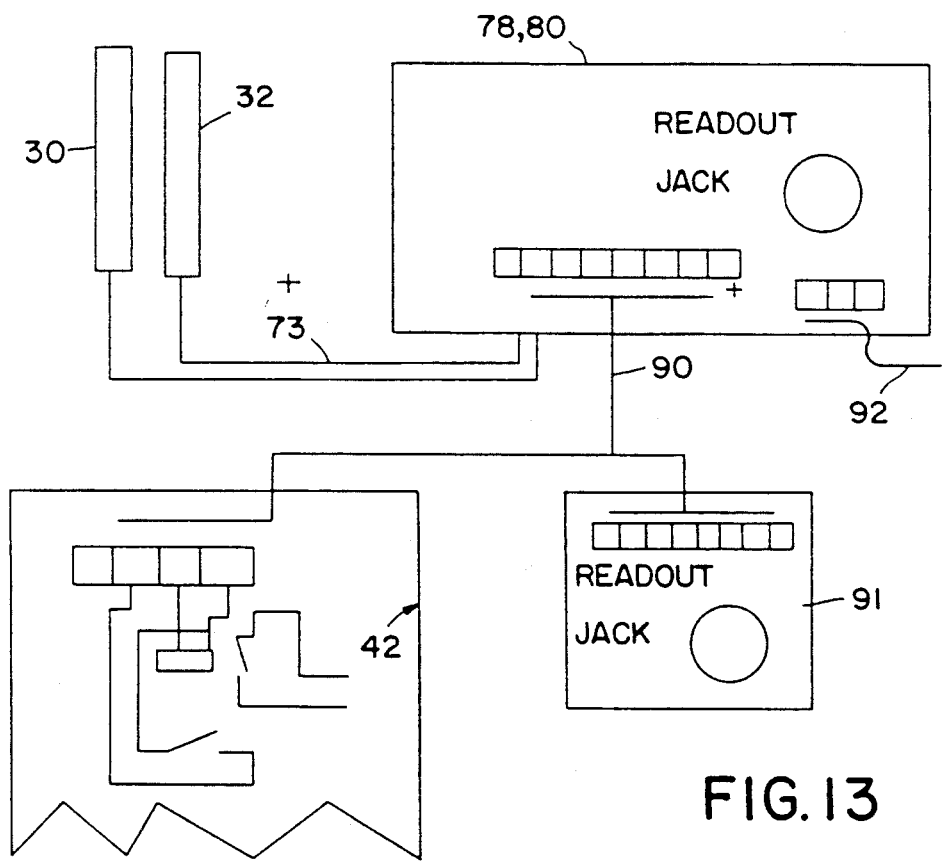
FIG. 13 is a schematic diagram of the electrode sensor illustrating a local and remote read-out.

Referring to FIG. 13, digital monitor and controller 40 includes the modules of FIG. 8 connected to electrodes 30 and 32 via a standard HF/HV cable 73. A remote read-out terminal jacks 91 is connected by an eight or twelve conductor cable 90 to a local terminal of the sensor of receiver 80. In the space being purified is a shut off device or plenum sensor 42 that senses the difference in air pressure for shutting down the system in the event that fan 12 should stop flowing the air.

It will be apparent to those skilled in the art that various modifications and variations can be made in the air purification system of the present invention without departing from the scope or spirit of the invention. For example, all electrode information may be connected to digital signals, i.e., D.C. voltage, A.C., voltage and frequency, capitance of grid which would be reset from a digital feedback loop (relative). System changes may be controlled from varying output circuits to match load characteristics. All inputs may be alarmed and transmitted to a printer and CRT. Operational and ambient data can be stored and trend log all information locally or remotely.

Thus, it is intended that the present invention covers the modifications and variations of this invention provided they come within the scope of the appended claims and their equivalents.

What we claim is:
1. An air purification system, comprising:
   means including a passage for flowing air to be purified;
   filtering means for filtering the flowing air in the passage;
   a power generator for generating a D.C. voltage in the kilovolt range and an A.C. voltage in the kilohertz range;
   a first electrode disposed in the flowing air passage and electrically connected to the power generator for creating a first portion of a complex electrical field having a D.C. voltage in the kilovolt range;
   a second electrode disposed in the flowing air passage adjacent the first electrode and electrically connected to the power generator for creating a second portion of the complex electrical field having an A.C. voltage in the kilohertz frequency range; and electrode detecting and monitoring means electrically connected directly to the first and second electrodes and responsive to the kilovolts and kilohertz of the first and second electrodes for outputting low D.C. voltage signals having values in the sensing range corresponding to the high D.C. and A.C. voltages of the electrodes in the kilovolt and kilohertz range, respectively.

2. The system of claim 1 further comprising an outlet connected to the output D.C. voltages for removably connecting terminals of a read-out device.

3. The system of claim 1, wherein the electrode detecting and monitoring means is operative to vary the frequency and high voltage of the power generator in accordance with the value of the D.C. output voltage signals of the electrode detecting and monitoring means.

4. The system of claim 1 wherein the electrode detecting and monitoring means comprises first circuit means, including means for generating a first output A.C. voltage having an RMS amplitude corresponding to a predetermined fraction of the RMS value of the high frequency A.C. voltage of the second electrode, means for generating a second output D.C. voltage signal having an amplitude corresponding to a predetermined fraction of the amplitude of the high D.C. voltage of the first electrode; and second circuit means including first converter means responsive to the first output A.C. voltage for generating a third output D.C. signal having a voltage amplitude corresponding to the RMS voltage of the second electrode, second converter means responsive to the fractional first output A.C. voltage for generating a fourth output D.C. signal having a voltage amplitude corresponding to the frequency of the A.C. voltage of the second electrode; the second, third, and fourth output D.C. signals constituting the low D.C. voltage signals in the sensing range.

5. The system of claim 4 wherein the means for generating the second output D.C. voltage is a voltage divider operative to generate a D.C. voltage corresponding to the kilovolt range in the sensing range of from approximately zero to two volts.

6. The system of claim 4 wherein the means for generating the third output D.C. voltage signal is a monolithic RMS to D.C. converter operative to output a D.C. voltage signal in the range of approximately zero to two volts.

7. The system of claim 4 wherein the means for generating the fourth output D.C. voltage signal is a frequency to voltage converter operative to output a D.C. voltage signal in the range of approximately zero to two volts.

8. The system of claim 4 wherein the first circuit means includes a first unitary circuit board, and the second circuit means includes a second unitary circuit board wire connected to the first unitary circuit board.

9. The system of claim 4, wherein the electrode detecting and monitoring means is operative to control the power supply generator in accordance with the value of the D.C. output voltage signals.

10. The system of claim 4, wherein the air flowing means includes a duct having an access door; the electrode detecting and monitoring means includes a safety door switch indicating the open and closed position of the access door and means operative to connect electrically the power generator to the first and second electrodes in accordance with the open and closed position of the access door.

11. The system of claim 1 wherein the electrode detecting and monitoring means directly connected to the second electrode includes first circuit means for generating an output A.C. voltage having an RMS amplitude corresponding to a predetermined fraction of the RMS value of the high frequency A.C. voltage of the second electrode; and second circuit means including converter means responsive to the first output A.C. voltage for generating an output D.C. signal having a voltage amplitude corresponding to the output A.C. voltage.

12. The system of claim 11 wherein the means connected to the second electrode for generating the output D.C. voltage signal is a monolithic RMS to D.C. converter operative to output a D.C. voltage signal in the zero to approximately two volt range.

13. The system of claim 11 wherein the electrode detecting and monitoring means further includes second converter means responsive to the output A.C. voltage for generating an output D.C. signal having a voltage amplitude corresponding to the frequency of the A.C. voltage of the second electrode.

14. The system of claim 13 wherein the electrode detecting and monitoring means connected to the second electrode includes a frequency to voltage converter operative to output a D.C. voltage signal in the range of approximately zero to two volts.

15. The system of claim 1 wherein the electrode detecting and monitoring means directly connected to the first electrode means, includes means for generating an output D.C. voltage signal having on amplitude corresponding to a predetermined fraction of the high D.C. voltage of the first electrode.

16. The system of claim 15 wherein the electrode detecting and monitoring means connected to the first electrode for generating the output D.C. voltage is a voltage divider operative to generate a D.C. voltage signal, corresponding to the kilovolt range, having a value in the sensing range of from zero to approximately two volts.

17. A method of air purification comprising:
flowing in a passage the air to be purified;
filtering the flowed air;
generating a high D.C. voltage in the kilovolt range and an A.C. voltage having a high frequency in the kilohertz range;
applying the generated D.C. voltage and A.C. voltage to respective first and second electrodes for creating a complex electrical field in the path of the flowed air;
detecting at the first and second electrodes the corresponding high frequency and high voltage of the complex electrical field;
reducing the detected high D.C. voltage to a first output D.C. voltage signal in the approximate range of zero to two volts;
reducing the detected high frequency A.C. voltage to a second D.C. voltage signal in the approximate range of 0 to 2 volts to correspond to the RMS of the A.C. voltage, and to a third D.C. voltage signal in the approximate range of zero to two volts to correspond to the frequency of the A.C. voltage; and
controlling the applied D.C. and A.C. voltages in accordance with the D.C. output voltage signals.

18. The method of claim 17, wherein the step of controlling includes varying selectively the frequency and high voltage of the generated power.

19. The method of claim 17, further comprising measuring at least one of the parameters of the group consisting of ion concentration, particulates, chemical composition, space charge, and duct humidity of the flowing air.

20. The method of claim 19, further comprising measuring the electrostatic characteristics of the air being treated.

* * * * *